(12) United States Patent
Coleman et al.

(10) Patent No.: US 7,842,025 B2
(45) Date of Patent: *Nov. 30, 2010

(54) DUAL-FUNCTION CATHETER HANDLE

(75) Inventors: James Coleman, Rialto, CA (US);
Claudio Plaza, Chino, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/369,670

(22) Filed: Feb. 11, 2009

(65) Prior Publication Data

US 2009/0149805 A1 Jun. 11, 2009

Related U.S. Application Data

(60) Division of application No. 11/173,105, filed on Jul. 1, 2005, now Pat. No. 7,503,914, which is a continuation of application No. 10/040,981, filed on Dec. 31, 2001, now Pat. No. 6,913,594.

(51) Int. Cl.
*A61M 25/00* (2006.01)
*A61B 6/00* (2006.01)

(52) U.S. Cl. ...................................... 604/528; 600/434

(58) Field of Classification Search .................. 604/523, 604/525, 528, 93.01, 95.04, 95.01; 600/433–5
See application file for complete search history.

(56) References Cited

U.S. PATENT DOCUMENTS

| | | | |
|---|---|---|---|
| 5,030,204 A | 7/1991 | Badger et al. | |
| 5,275,151 A | 1/1994 | Shockey et al. | |
| 5,462,527 A | 10/1995 | Stevens-Wright et al. | |
| 5,527,279 A | 6/1996 | Imran | |
| 5,611,777 A | 3/1997 | Bowden et al. | |
| 5,662,606 A | 9/1997 | Cimino et al. | |
| 5,741,320 A | 4/1998 | Thornton et al. | |
| 5,906,483 A | 5/1999 | Zhou | |

(Continued)

FOREIGN PATENT DOCUMENTS

WO    WO 97/07848 A1    3/1997

OTHER PUBLICATIONS

European Search Report for EP 02 25 9037 dated Dec. 8, 2003.

*Primary Examiner*—Kevin C Sirmons
*Assistant Examiner*—Catherine N Witczak
(74) *Attorney, Agent, or Firm*—Christie, Parker & Hale, LLP

(57) ABSTRACT

A dual function catheter handle for simultaneous movement of two control wires has a handle housing having a core with a longitudinal slot mounted in its interior. A first moveable member is provided with a proximal end mounted in the interior of the handle housing and a distal end extending outside the handle housing. The first moveable member is longitudinally moveable relative to the handle housing. A second moveable member is mounted in the longitudinal slot of the core and is longitudinally moveable relative to the core and handle housing. A rotatable member is mounted on the handle housing and has a threaded inner surface that mates with a threaded surface of the second moveable member so that rotation of the rotatable member causes longitudinal movement of the second moveable member. The first and second moveable members can simultaneously move proximally relative to the handle housing.

9 Claims, 10 Drawing Sheets

U.S. PATENT DOCUMENTS

| | | |
|---|---|---|
| 5,987,344 A | 11/1999 | West |
| 6,027,462 A | 2/2000 | Greene et al. |
| 6,059,739 A | 5/2000 | Baumann |
| 6,156,027 A | 12/2000 | West |
| 6,171,277 B1 | 1/2001 | Ponzi |
| 6,183,435 B1 | 2/2001 | Bumgalough et al. |
| 6,198,974 B1 | 3/2001 | Webster, Jr. et al. |
| 6,263,224 B1 | 7/2001 | West |
| 6,913,594 B2 * | 7/2005 | Coleman et al. ......... 604/95.04 |
| 7,503,914 B2 * | 3/2009 | Coleman et al. ............ 604/528 |

* cited by examiner

DUAL-FUNCTION CATHETER HANDLE

CROSS-REFERENCE TO RELATED APPLICATION(S)

This application is a divisional application of U.S. patent application Ser. No. 11/173,105, filed Jul. 1, 2005 now U.S. Pat. No. 7,503,914, entitled DUAL FUNCTION CATHETER HANDLE, which is a continuation of U.S. patent application Ser. No. 10/040,981, filed Dec. 31, 2001 now U.S. Pat. No. 6,913,594, entitled DUAL-FUNCTION CATHETER HANDLE, the entire disclosures of which are incorporated herein by reference.

FIELD OF THE INVENTION

The present invention is directed to a dual-function catheter handle for manipulating two different control wires.

BACKGROUND OF THE INVENTION

Electrode catheters have been in common use in medical practice for many years. They are used to stimulate and map electrical activity in the heart and to ablate sites of aberrant electrical activity.

In use, the electrode catheter is inserted into a major vein or artery, e.g., femoral artery, and then guided into the chamber of the heart which is of concern. Within the heart, the ability to control the exact position and orientation of the catheter tip is critical and largely determines how useful the catheter is.

Steerable catheters are generally well-known. For example, U.S. Pat. No. RE 34,502 describes a catheter having a control handle comprising a housing having a piston chamber at its distal end. A piston is mounted in the piston chamber and is afforded lengthwise movement. The proximal end of the catheter body is attached to the piston. A puller wire is attached to the housing and extends through the piston and through the catheter body. The distal end of the puller wire is anchored in the tip section of the catheter. In this arrangement, lengthwise movement of the piston relative to the housing results in deflection of the distal end of the catheter body. The design described in RE 34,502 is generally limited to a catheter having a single puller wire.

Some catheter designs require more than one puller wire. For example, if a bidirectional catheter is desired, i.e., a catheter that can be deflected in more than one direction without rotating the catheter body, more than one puller wire becomes necessary. Catheters having two or more puller wires and handles for controlling the multiple puller wires are disclosed, for example, in U.S. Pat. Nos. 6,171,277 and 6,183,463. However, these patents describe catheter handles whereby simultaneous proximal movement of the puller wires relative to the catheter body is prohibited, which is desirable for certain applications. However, for other applications, it is desirable to simultaneously move the puller wires proximally relative to the catheter body.

SUMMARY OF THE INVENTION

The present invention is directed to a dual function catheter handle that is capable of simultaneously moving two control or puller wires relative to the body of the catheter and also to a catheter incorporating the handle. In one embodiment, the invention is directed to a catheter handle comprising a handle housing having proximal and distal ends and a generally hollow interior. A first moveable member is provided having a proximal end mounted in the interior of the handle housing and a distal end extending outside the handle housing. The first moveable member is longitudinally moveable relative to the handle housing. A second moveable member is mounted in the interior of the handle housing and longitudinally moveable relative to the handle housing. A rotatable member is mounted on the handle housing so that rotation of the rotatable member causes longitudinal movement of the second moveable member.

In a particularly preferred embodiment, the invention is directed to a catheter handle comprising a handle housing having proximal and distal ends and a generally hollow interior. A core is mounted in the interior of the handle housing, the core having a longitudinal slot therethrough. A first moveable member is provided having a proximal end mounted in the interior of the handle housing and a distal end extending outside the handle housing. The first moveable member is longitudinally moveable relative to the handle housing. A second moveable member is mounted in the longitudinal slot of the core and is longitudinally moveable relative to the core and handle housing. The second moveable member has a threaded surface. A rotatable member is mounted on the handle housing and has a threaded inner surface that mates with the threaded surface of the second moveable member. Rotation of the rotatable member causes longitudinal movement of the second moveable member.

In another embodiment, the invention is directed to a catheter incorporating the inventive handle. The catheter comprises an elongated, flexible catheter body having proximal and distal ends and a lumen extending therethrough. An intermediate section is mounted at the distal end of the catheter body. The intermediate section has proximal and distal ends and first and second off-axis lumens extending therethrough. The intermediate section can be separate from or integral with the catheter body. A handle as described above is mounted at the proximal end of the catheter body. The catheter body is attached to the handle housing, either directly or indirectly, for example, by mounting it to the core. A first puller wire extends through the catheter body and first off-axis lumen of the intermediate section. The first puller wire has a proximal end anchored to the first moveable member of the handle and a distal end anchored at or near the distal end of the catheter. The distal end of the catheter to which the puller wires are anchored can include any part of the distal end that is inserted into the heart, such as the intermediate section or another ablation or mapping assembly that is mounted onto the intermediate section. A second puller wire extends through the catheter body and second off-axis lumen of the intermediate section. The second puller wire has a proximal end anchored to the second moveable member of the handle and a distal end anchored at or near the distal end of the catheter. In a particularly preferred embodiment, the distal end of the first puller wire is anchored to the intermediate section and the catheter further comprises a generally circular mapping assembly mounted on distal end of the intermediate section, wherein the distal end of the second puller wire extends through an off-axis lumen of them mapping assembly and is anchored at or near the distal end of the mapping assembly for contraction of the mapping assembly.

DESCRIPTION OF THE DRAWINGS

These and other features and advantages of the present invention will be better understood by reference to the following detailed description when considered in conjunction with the accompanying drawings wherein.

DETAILED DESCRIPTION OF THE INVENTION

Figure 1:
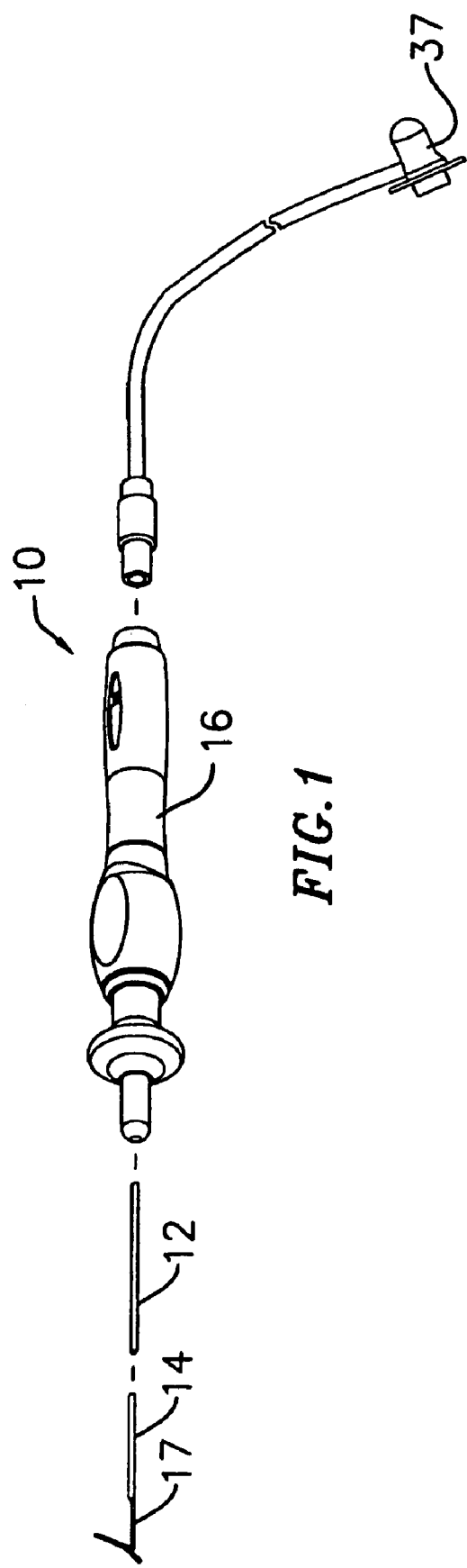
FIG. 1 is a perspective view of a catheter according to the invention.

The invention is directed to a catheter handle for manipulating two independently displaceable control or puller wires. FIG. 1 shows a catheter 10 comprising an elongated catheter body 12 having proximal and distal ends, a control handle 16 attached at the proximal end of the catheter body, an intermediate section 14 attached at the distal end of the catheter body, and a mapping assembly 17 attached to the intermediate section.

Figure 2:
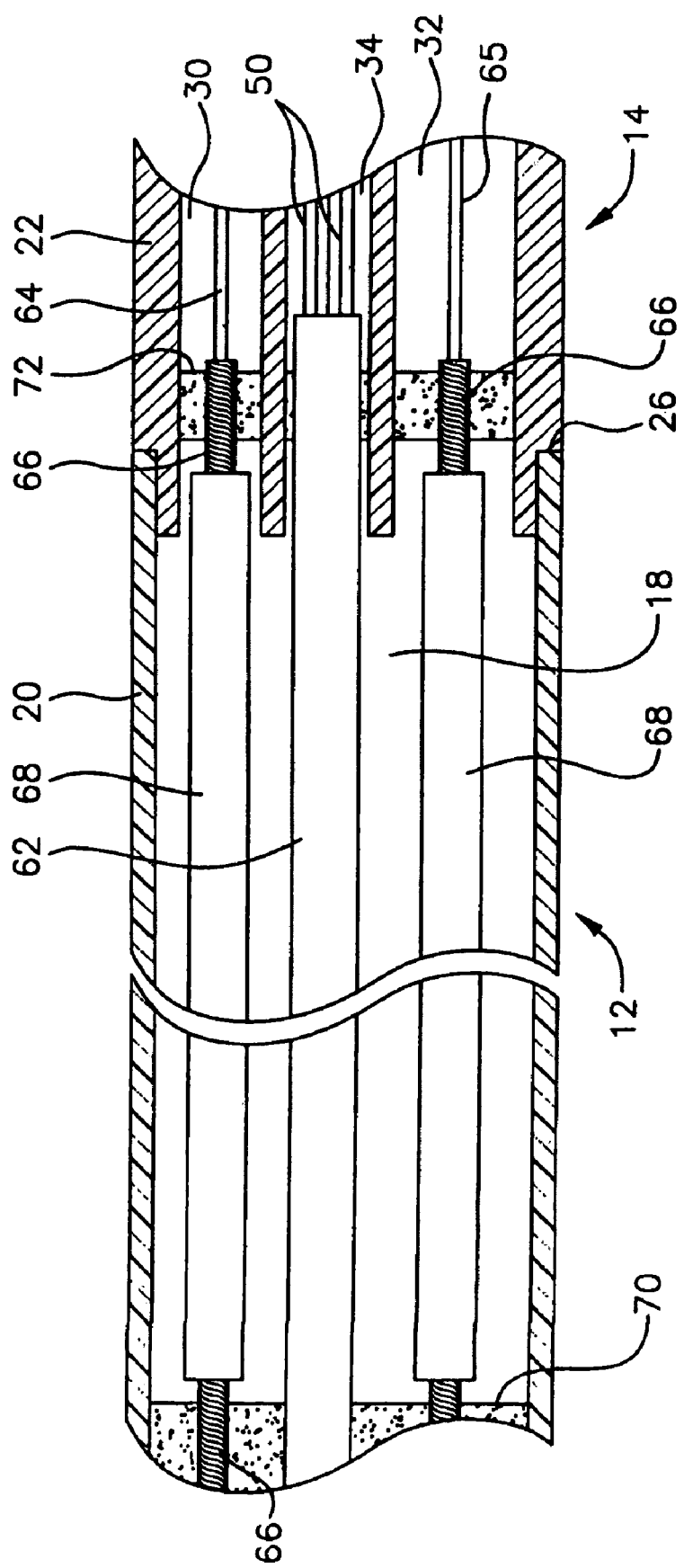
FIG. 2 is a side cross-sectional view of the catheter body of a catheter according to the invention.

With reference to FIG. 2, the catheter body 12 comprises an elongated tubular construction having a single, axial or central lumen 18, although multiple lumens can be provided if desired. The catheter body 12 is flexible, i.e., bendable, but substantially non-compressible along its length. The catheter body 12 can be of any suitable construction and made of any suitable material. A presently preferred construction comprises an outer wall 20 made of polyurethane or PEBAX. The outer wall 20 comprises an imbedded braided mesh of stainless steel or the like to increase torsional stiffness of the catheter body 12 so that, when the control handle 16 is rotated, the intermediate section 14 of the catheter 10 will rotate in a corresponding manner.

The outer diameter of the catheter body 12 is not critical, but is preferably no more than about 8 french, more preferably about 7 french. Likewise the thickness of the outer wall 20 is not critical, but is thin enough so that the central lumen 18 can accommodate a puller wire, lead wires, and any other desired wires, cables or tubes, as discussed in more detail below. If desired, the inner surface of the outer wall 20 may be lined with a stiffening tube (not shown) to provide improved torsional stability. A particularly preferred catheter has an outer wall 20 with an outer diameter of from about 0.090 inch to about 0.94 inch and an inner diameter of from about 0.061 inch to about 0.065 inch.

Figure 3:
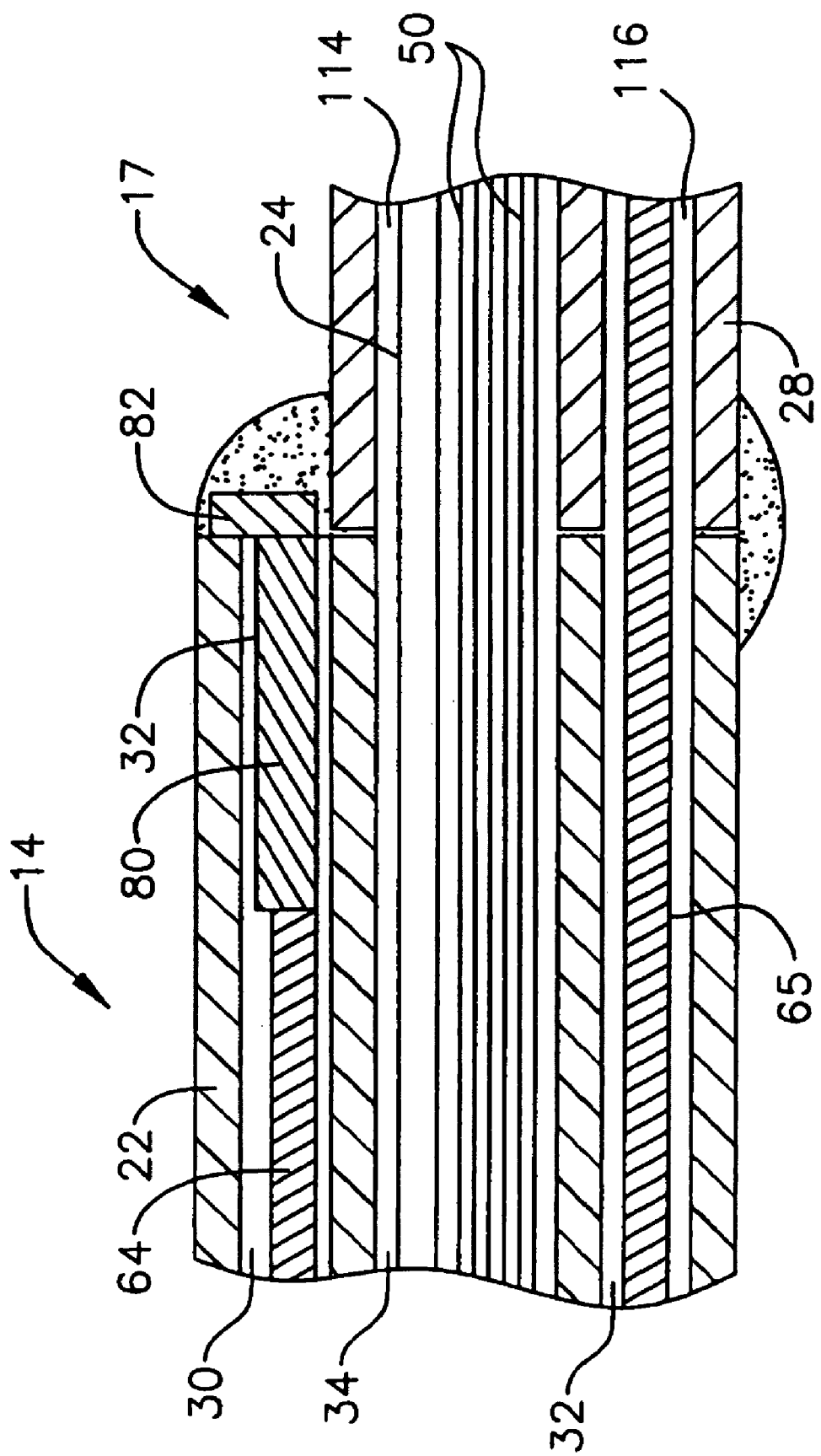
FIG. 3 is a side cross-sectional view of the junction of the intermediate section and mapping assembly of a catheter according to the invention.

As shown in FIGS. 2 and 3, the intermediate section 14 comprises a short section of tubing 22 having three off-axis lumens, a first lumen 30 that carries a first puller wire 64, a second lumen 32 that carries a second puller wire 65 and a third lumen 34 that carries electrode lead wires 50 and a support member 24 for the mapping assembly 17, all of which are discussed further below. The tubing 22 is made of a suitable non-toxic material that is preferably more flexible than the catheter body 12. A presently preferred material for the tubing 22 is braided polyurethane, i.e., polyurethane with an embedded mesh of braided stainless steel or the like. The size of each lumen is not critical, but is sufficient to house the lead wires, puller wire or support member.

The useful length of the catheter, i.e., that portion that can be inserted into the patient excluding the mapping assembly 17, can vary as desired. Preferably the useful length ranges from about 110 cm to about 120 cm. The length of the intermediate section 14 is a relatively small portion of the useful length, and preferably ranges from about 3.5 cm to about 10 cm, more preferably from about 5 cm to about 6.5 cm.

A preferred means for attaching the catheter body 12 to the intermediate section 14 is illustrated in FIG. 2. The proximal end of the intermediate section 14 comprises an outer circumferential notch 26 that receives the inner surface of the outer wall 22 of the catheter body 12. The intermediate section 14 and catheter body 12 are attached by glue or the like.

Alternatively, the catheter body 12 and intermediate section 14 can be formed of a single unitary piece of tubing. Such a design would be useful, for example, where the catheter body and intermediate section have the same number of lumens.

If desired, a spacer (not shown) can be located within the catheter body 12 between the distal end of the stiffening tube (if provided) and the proximal end of the intermediate section 14. The spacer provides a transition in flexibility at the junction of the catheter body 12 and intermediate section 14, which allows this junction to bend smoothly without folding or kinking. A catheter having such a spacer is described in U.S. Pat. No. 5,964,757, the disclosure of which is incorporated herein by reference.

At the distal end of the intermediate section 14 is a mapping assembly, as shown in FIGS. 3 to 7. The mapping assembly comprises a non-conductive covering 28 having two off-axis lumens 114 and 116 extending therethrough. The distal end of the support member 24, which gives shape to the mapping assembly 17, extends through the first lumen 114 of the non-conductive covering 28. However, if desired, the support member 24 can be eliminated and the non-conductive covering 28 can be designed to provide the desired shape for the mapping assembly 17.

The mapping assembly 17 has a generally straight proximal region 38, a generally circular main region 39 and a generally straight distal region 40. The proximal region 38 is mounted on the intermediate section 14, as described in more detail below, so that its axis is generally parallel to the axis of the intermediate section. The proximal region 38 preferably has an exposed length, e.g., not contained within the intermediate section 14, ranging from about 3 mm to about 12 mm, more preferably about 3 mm to about 8 mm, still more preferably about 5 mm inch, but can vary as desired.

Figure 4:
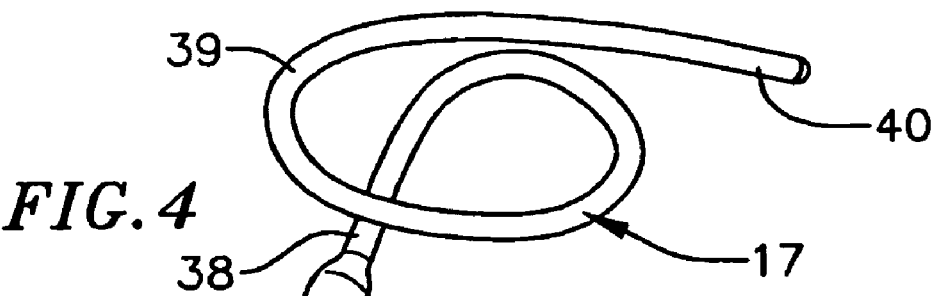
FIG. 4 is a schematic perspective view of the mapping assembly according to the invention.
Figure 5:
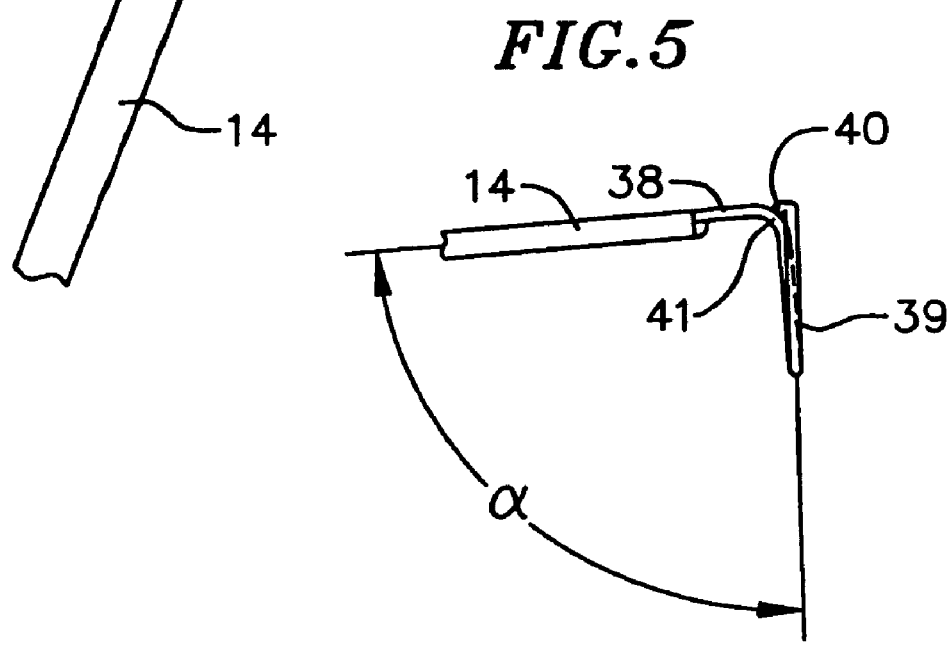
FIG. 5 is a side view of the mapping assembly according to the invention in a clockwise formation.
Figure 6:
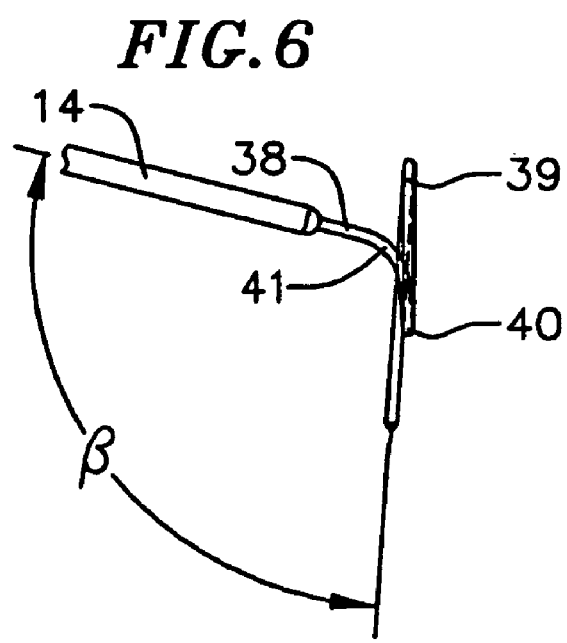
FIG. 6 is a side view of the mapping assembly according to the invention in a counterclockwise formation rotated 90° relative to the assembly depicted in FIG. 5.

The generally circular main region 39 does not form a flat circle, but is very slightly helical, as shown in FIGS. 4 to 6. The main region 39 has an outer diameter preferably ranging from about 8 mm to about 35 mm, more preferably from about 12 mm to about 20 mm, still more preferably about 15 mm. The transition region 41 of the straight proximal region 38 and generally circular main region 39 is slightly curved and formed such that, when viewed from the side with the proximal region at the top of the circular main region as shown in FIG. 5, the proximal region (along with the intermediate section 14) forms an angle α with the curved region ranging from about 75° to about 95°, preferably from about 83° to about 93°, more preferably about 87°. The main region 39 can curve in a clockwise direction, as shown in FIG. 5, or a counterclockwise direction, as shown in FIG. 6. When the assembly 17 is turned 90°, as shown in FIG. 6, so that the transition region 41 is near the center of the main region, the proximal region (along with the intermediate section 14) forms an angle β with the main region ranging from about 90° to about 135°, preferably from about 100° to about 110°, more preferably about 105°.

The support member 24 is made of a material having shape memory, i.e., that can be straightened or bent out of its original shape upon exertion of a force and is capable of substantially returning to its original shape upon removal of the force. A particularly preferred material for the support member 24 is a nickel/titanium alloy. Such alloys typically comprise about 55% nickel and 45% titanium, but may comprise from about 54% to about 57% nickel with the balance being titanium. A preferred nickel/titanium alloy is Nitinol, which has excellent shape memory, together with ductility, strength, corrosion resistance, electrical resistivity and temperature stability. The non-conductive covering 28 can be made of any suitable material, and is preferably made of a biocompatible plastic such as polyurethane or PEBAX.

A series of ring electrodes 36 are mounted on the non-conductive covering 28 of the generally circular main region 39 of the mapping assembly 17. The ring electrodes 36 can be made of any suitable solid conductive material, such as platinum or gold, preferably a combination of platinum and iridium, and mounted onto the non-conductive covering 28 with glue or the like. Alternatively, the ring electrodes can be formed by coating the non-conductive covering 28 with an electrically conducting material, like platinum, gold and/or iridium. The coating can be applied using sputtering, ion beam deposition or an equivalent technique.

In a preferred embodiment, each ring electrode 36 is mounted by first forming a hole in the non-conductive covering 28. An electrode lead wire 50 is fed through the hole, and the ring electrode 36 is welded in place over the lead wire and non-conductive covering 28. The lead wires 50 extend between the non-conductive covering 28 and the support member 24.

Figure 7:
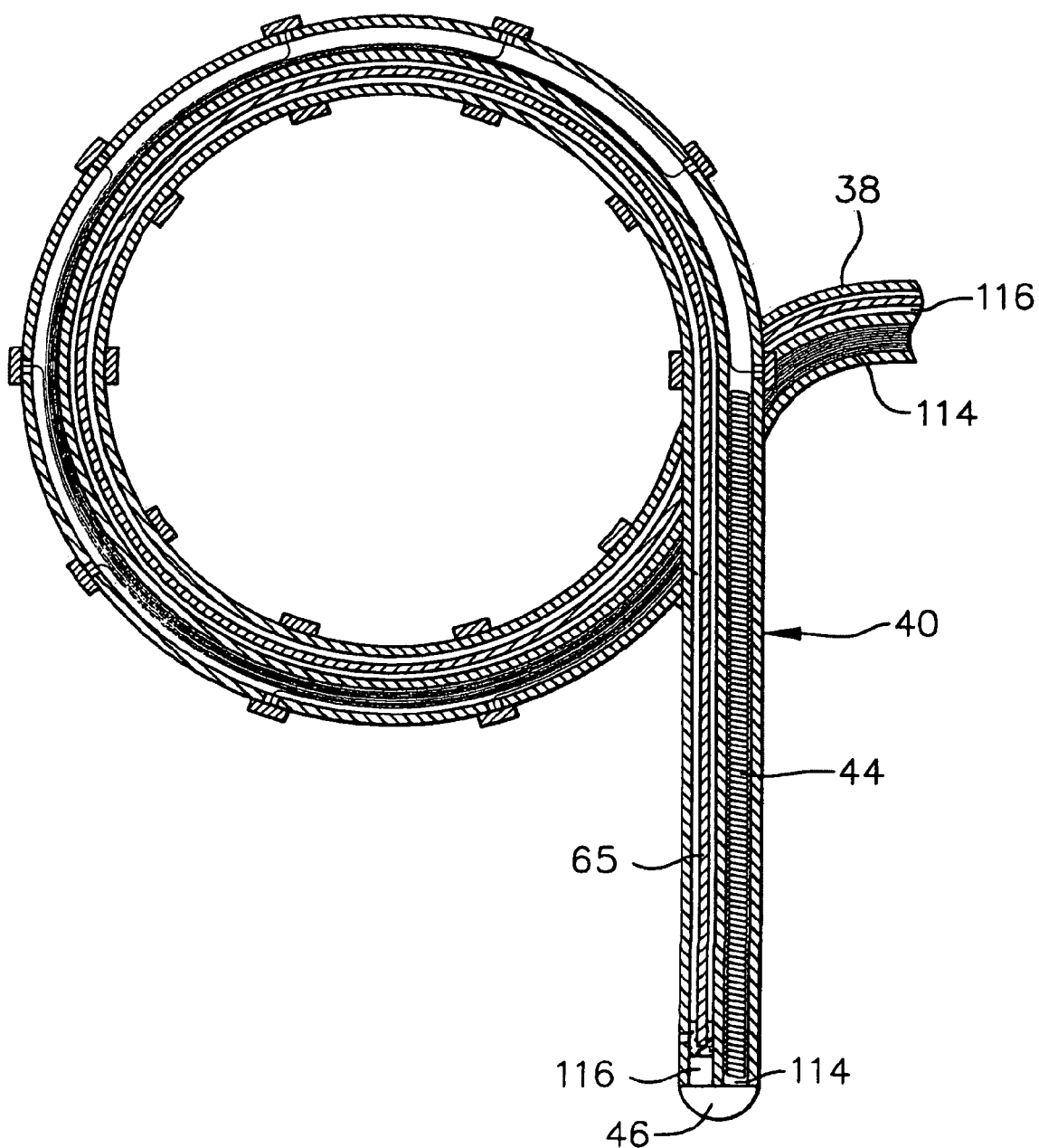
FIG. 7 is a schematic view of the mapping assembly according to the invention.

The number of ring electrodes 36 on the assembly can vary as desired. Preferably the number of ring electrodes ranges from about six to about twenty, more preferably from about eight to about twelve. In a particularly preferred embodiment, the assembly carries ten ring electrodes. The ring electrodes 36 are preferably approximately evenly spaced around the generally circular main region 39, as best shown in FIG. 7. In a particularly preferred embodiment, a distance of approximately 5 mm is provided between the centers of the ring electrodes 36.

Figure 8:
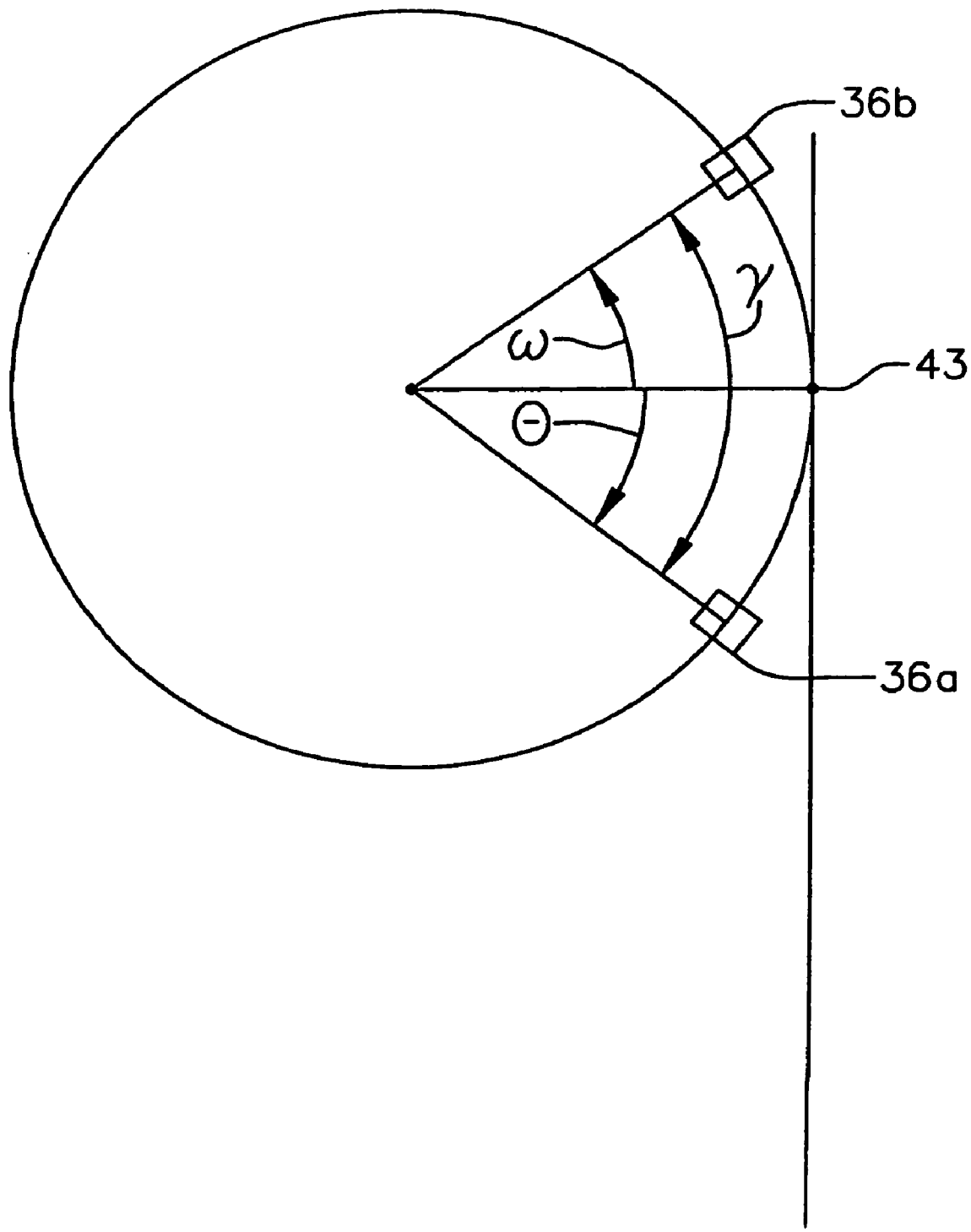
FIG. 8 is a schematic view of the mapping assembly according to the invention depicting the relationship between the first and last electrodes.

FIGS. 7 and 8 show a particularly preferred electrode arrangement. As explained above, the generally circular main region 39 is very slightly helical, although FIGS. 7 and 8 depict the main region as a flat circle, as it would generally appear when viewed from the distal end of the catheter. The generally straight distal region 40 forms a tangent relative to the generally circular main region 39 and contacts the main region at a tangent point 43. A first electrode 36a is provided, which is the electrode that is on the generally circular main region 39 closest to the proximal region 38. A second electrode 36b is provided, which is the electrode that is on the generally circular main region 39 closest to the distal region 40. Preferably, the first electrode 36a is positioned along the circumference of the generally circular main region 39 at a distance θ of no more than about 55° from the tangent point, more preferably no more than about 48° from the tangent point, still more preferably from about 15° to about 36° from the tangent point.

Preferably the second electrode 36b is positioned along the circumference of the generally circular main region 39 at a distance ω of no more than about 55° degrees from the tangent point, more preferably no more than about 48° from the tangent point, still more preferably from about 15° to about 36° from the tangent point. Preferably the first electrode 36a is positioned along the circumference of the generally circular main region 39 at a distance γ of no more than 100° from the second electrode 36b, preferably no more than 80° from the second electrode, still more preferably from about 30° to about 75° from the second electrode. If desired, additional electrodes (not shown) could be mounted along the intermediate section 14, the generally straight proximal section 39, the transition region 41, and/or generally straight distal region 40.

The junction of the intermediate section 14 and mapping assembly 17 is shown in FIG. 3. The non-conductive covering 28 is attached to the tubing 22 of the intermediate section by glue or the like. The support member 24 extends from the third lumen 34 into the first lumen 114 of the non-conductive covering 28 and through the generally circular main region 39 of the mapping assembly. The proximal end of the support member 24 terminates a short distance within the third lumen 34 of the intermediate section 14, approximately about 5 mm, so as not to adversely affect the ability of the intermediate section to deflect. However, if desired, the proximal end of the support member 24 can extend into the catheter body 12.

The lead wires 50 attached to the ring electrodes 36 also extend through the first lumen 114 in the non-conductive covering 28, the third lumen 34 of the intermediate section 14, the central lumen 18 of the catheter body 12, and the control handle 16, and terminate at their proximal end in the connector 37, which is connected to a source of RF energy (not shown). The portion of the lead wires 50 extending through the central lumen 18 of the catheter body 12, control handle 16 and proximal end of the intermediate section 14 are enclosed within a protective sheath 62, which can be made of any suitable material, preferably polyimide. The protective sheath 62 is anchored at its distal end to the proximal end of the intermediate section 14 by gluing it in the third lumen 34 with polyurethane glue or the like.

The generally straight distal region 40 of the mapping assembly 17 is provided with an atraumatic design to prevent the distal end of the mapping assembly from penetrating tissue. In the depicted embodiment, the distal region 40 comprises a tightly wound coil spring 44 made, for example, of stainless steel, such as the mini guidewire commercially available from Cordis Corporation (Miami, Fla.) or a coil having a 0.0045 inch wire size and a 0.009 inch inner diameter, such as that commercially available from Microspring. The coil spring 44 extends through the first lumen 114 of the non-conductive covering 28 and is mounted at its proximal end in a short piece of tubing 45 with polyurethane glue or the like, which is then glued or otherwise anchored within the non-conductive covering. The tubing 45 is less flexible than the non-conductive covering 28 but more flexible than that support member 24 to provide a transition in flexibility along the length of the mapping assembly 17. The distal end of the distal region 40 is capped, preferably with polyurethane glue 46, to prevent body fluids from entering the mapping assembly 17. In the depicted embodiment, the generally straight distal region 40 has a length of about 0.5 inch, but can be any desired length, for example, ranging from about 0.25 inch to about 1.0 inch. The generally straight distal region 40 is preferably sufficiently long to serve as an anchor for introducing the catheter into a guiding sheath, as discussed in more detail below, because the mapping assembly 17 must be straightened upon introduction into the sheath. Without having the generally straight distal region 40 as an anchor, the mapping assembly 17 has a tendency to pull out of the guiding sheath upon its introduction into the guiding sheath. Additionally, if desired, the distal region 40 can be formed, at least in part, of a radiopaque material to aid in the positioning of the mapping assembly 17 under fluoroscopy.

As noted above, two puller wires 64 and 65 extend through the catheter. The first puller wire 64 is provided for deflection of the intermediate section 14. The second puller wire 65 is provided for contracting the mapping assembly 17. Each puller wire 64 and 65 extends from the control handle 16, through the central lumen 18 of the catheter body 12 and into the first and second lumens 30 and 32 of the intermediate section 14, respectively. The second puller wire 65 then extends into the second lumen 116 of the mapping assembly 17. As described in more detail below, the proximal end of the first puller wire 64 is anchored within the control handle 16, and the distal end of the first puller wire is anchored in the intermediate section 14. Also as described further below, the proximal end of the second puller wire 65 is anchored within the control handle 16, and the distal end of the second puller wire is anchored in the distal end of the mapping assembly 17.

Each puller wire 64 and 65 is made of any suitable metal, such as stainless steel or Nitinol. Preferably each puller wire 64 and 65 has a coating (not shown), such as a coating of Teflon or the like. Each puller wire 64 and 65 has a diameter preferably ranging from about 0.006 inch to about 0.010 inch.

In the depicted embodiment, the first puller wire 64 is anchored at its distal end to the distal end of the intermediate section 14 using a T-shaped anchor, as shown in FIG. 3, which comprises a short piece of tubular stainless steel 80, e.g., hypodermic stock, which is fitted over the distal end of the first puller wire 64 and crimped to fixedly secure it to the first puller wire. The distal end of the tubular stainless steel 80 is fixedly attached, e.g., by welding, to a cross-piece 82 formed of stainless steel ribbon or the like. The cross-piece 82 sits beyond the distal end of the first lumen 30. The cross-piece 82 is larger than the lumen opening and, therefore, cannot be pulled through the opening. The distal end of the first lumen 30 is then filled with glue or the like, preferably a polyurethane glue. Within the first lumen 30 of the intermediate section 14, the first puller wire 64 extends through a plastic, preferably Teflon®, puller wire sheath (not shown), which prevents the first puller wire 64 from cutting into the wall of the intermediate section 14 when the intermediate section is deflected. Alternatively, the first puller wire 64 could be anchored to the side wall of the intermediate section 14 in a similar manner, where the T-shaped anchor extends into a notch in the side wall rather than beyond the distal end of the first lumen 30. Such a design is disclosed in U.S. Pat. No. 6,064,908, the disclosure of which is incorporated herein by reference.

The second puller wire 65 is anchored in the distal end of the second lumen 116 of the mapping assembly in a manner similar to the first puller wire 64. A T-shaped anchor is mounted on the distal end of the second puller wire 65, extends into a notch in the side wall of the non-conductive covering 28, and is held in place with polyurethane glue or the like. Any other suitable method for anchoring the puller wires 64 and 65 could also be used.

In the depicted embodiment, two compression coils 66 are situated within the catheter body 12, each in surrounding relation to a corresponding puller wire 64 and 65. Each compression coil 66 extends from the proximal end of the catheter body 12 to the proximal end of the intermediate section 14. The compression coils 66 are made of any suitable metal, preferably stainless steel. Each compression coil 66 is tightly wound on itself to provide flexibility, i.e., bending, but to resist compression. The inner diameter of each compression coil 66 is preferably slightly larger than the diameter of the corresponding puller wire 64 and 65. The Teflon® coatings on the puller wire 64 allow them to slide freely within the compression coils 66. The outer surfaces of the compression coil 66 are covered by flexible, non-conductive sheathes 68, e.g., made of polyimide tubing.

Each compression coil 66 is anchored at its proximal end to the outer wall 20 of the catheter body 12 by proximal glue joint 70 and at its distal end to the intermediate section 14 by distal glue joint 72. Both glue joints 70 and 72 preferably comprise polyurethane glue or the like. The glue may be applied by means of a syringe or the like through a hole made between the outer surface of the catheter body 12 and the central lumen 18. Such a hole may be formed, for example, by a needle or the like that punctures the outer wall 20 of the catheter body 12 which is heated sufficiently to form a permanent hole. The glue is then introduced through the hole to the outer surfaces of the compression coils 66 and wicks around the outer circumferences to form a glue joint about the entire circumferences of the compression coils. If desired, the compression coils 66 could be anchored at different longitudinal locations or eliminated altogether.

Figure 9:
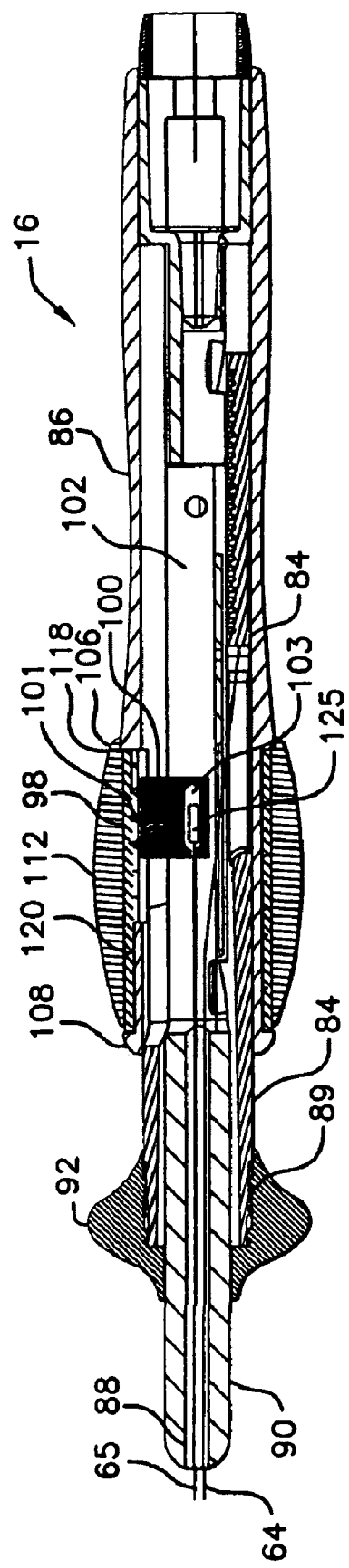
FIG. 9 is a side section view of a catheter handle according to the invention.
Figure 10:
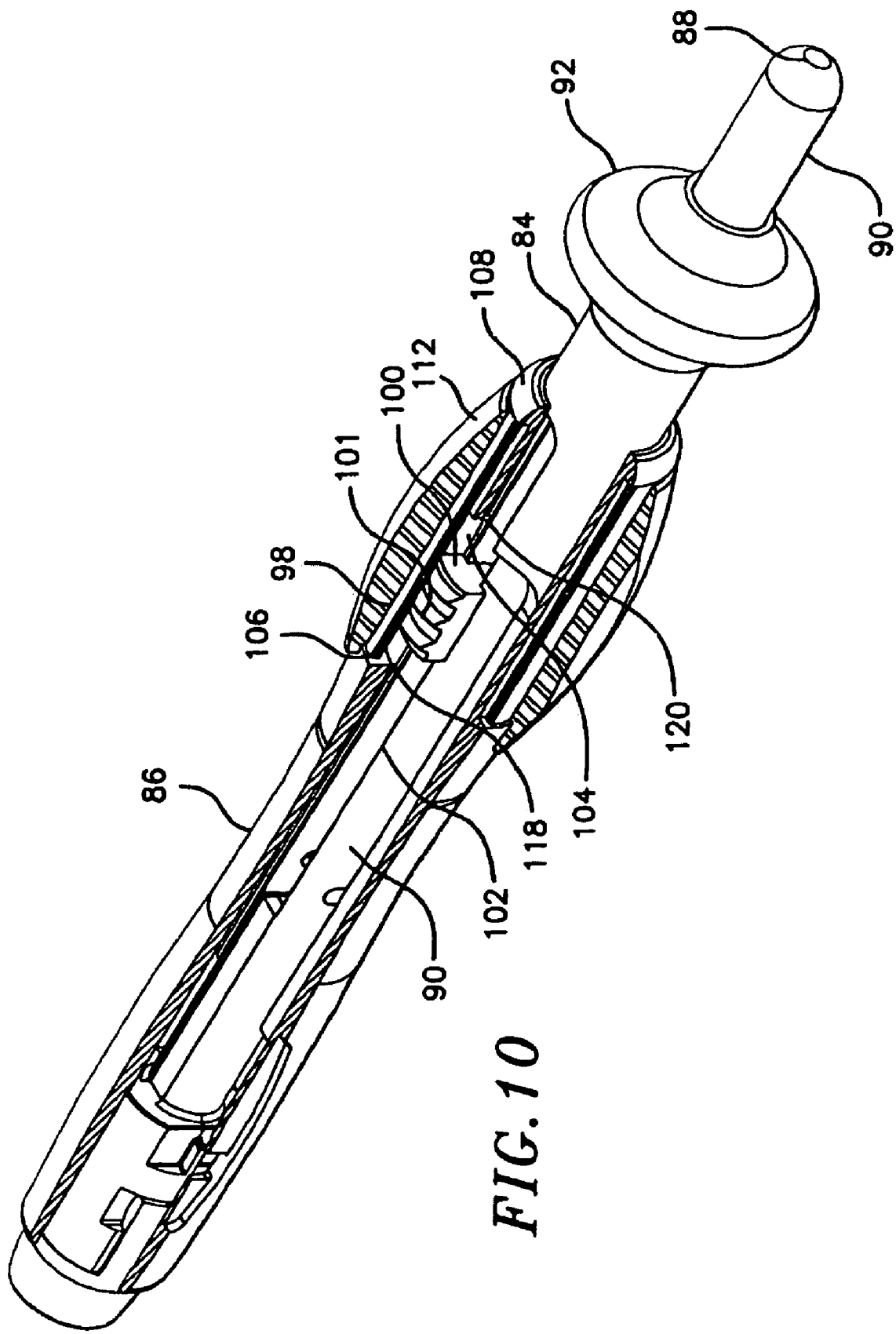
FIG. 10 is a cut away view of the catheter handle of FIG. 9.
Figure 11:
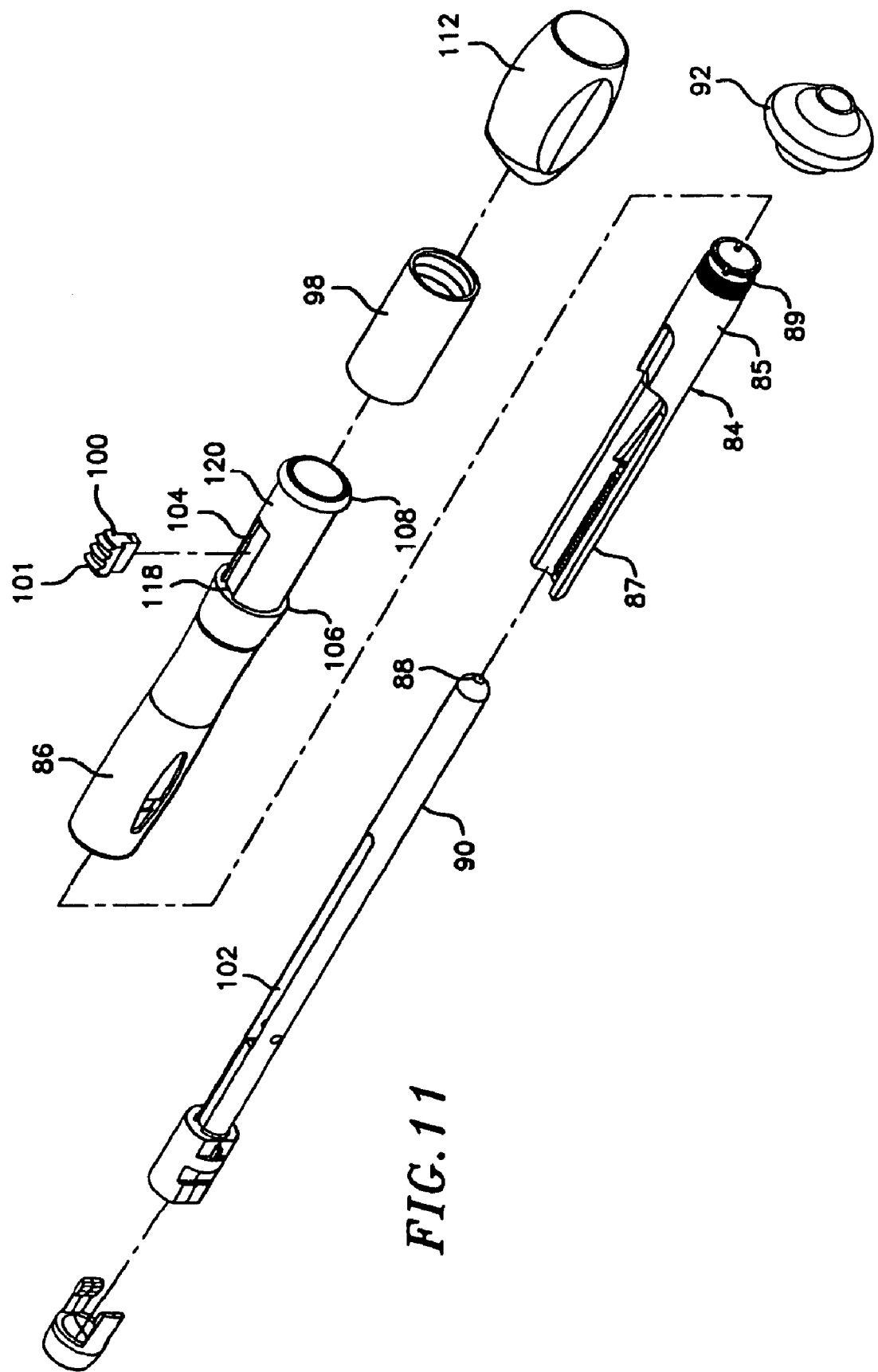
FIG. 11 is a perspective view of an assembly of the catheter handle of FIG. 9.

Longitudinal movement of each of the puller wires 64 and 65 relative to the catheter body 12 is accomplished by suitable manipulation of the control handle 16. An embodiment of the control handle 16 according to the invention is shown in FIGS. 9 to 11. The control handle 16 comprises a generally tubular housing 86 having a longitudinal axis and proximal and distal ends and a generally tubular core 90 extending within the housing along its longitudinal axis. In the depicted embodiment, the core 90 is a separate piece that is fixedly attached to the handle housing 86 for ease in manufacturing, although the core could be formed integral with the housing if desired. The core 90 has proximal and distal ends that extend beyond and outside the proximal and distal ends, respectively, of the housing 86. The catheter body 12 is fixedly attached to the distal end of the core 90 by means of a glue joint and shrink sleeve, as is generally known to those skilled in the art, or by any other suitable method. The puller wires 64 and 65, lead wires 50 and any other wires, tubes or cables that extend through the catheter body 12 extend through a lumen or passage 88 in the core 90, although the lead wires 50 are not shown in FIGS. 9 to 11 for clarity. An elongated slot 102 extends through a portion of the length of the core 90.

A piston 84 is mounted within the housing 86 in surrounding relation to the core 90. The piston 84 has a tubular distal end 85 and a semicircular proximal end 87. The semicircular proximal end 87 is shaped so that its inner surface fits generally against the tubular core 102. The precise shape of the piston 84 is not critical to the invention. When the handle 16 is assembled, a portion of the distal end 85 of the piston 84 extends outside the distal end of the handle housing 86. The distal end 85 of the piston 84 comprises threading 89 to provide a means for mounting a thumb control 92, having corresponding internal threading (not shown), onto the piston. A preferred arrangement for mounting the thumb control 92 on the piston 84 is described in U.S. patent application Ser. No. 09/546,310 filed Apr. 10, 2000, entitled "Single Gear Drive Bi-Directional Control Handle for Steerable Catheter," the disclosure of which is incorporated herein by reference. With this design, the user can cause longitudinal movement of the piston 84 relative to the handle housing 86 by pushing or pulling the piston 84 (directly or via the thumb control 92).

Figure 12:
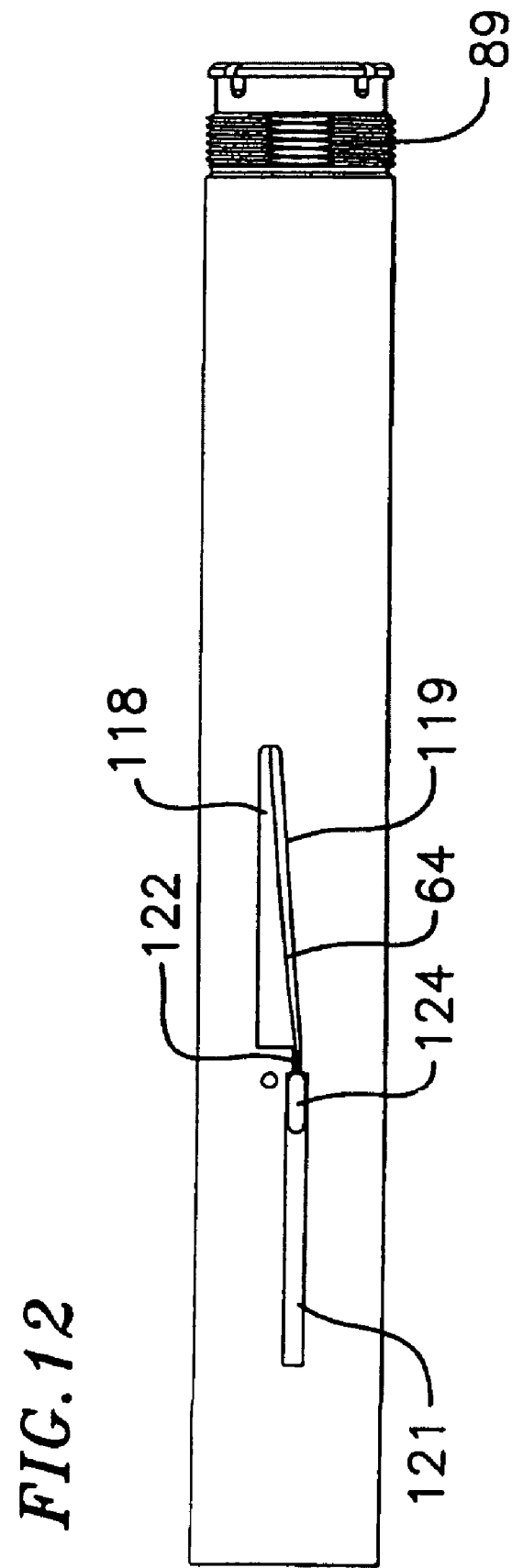
FIG. 12 is a perspective view of the piston of the catheter handle of FIG. 9.

The proximal end of the first puller wire 64 is anchored to the piston 84 by any suitable method. In the depicted embodiment, as shown in FIG. 12, the proximal end of the piston 84 comprises a generally rectangular opening 118 having a slanted edge 119. The opening 118 extends through a wall of the piston 84. A channel 121, which only extends a part of the way through the wall of the piston 84, is provided proximal the opening 118. A small groove 122 having a width less than that of the channel 121 connects the channel to the opening 118. The first puller wire 64 extends through the lumen 88 in the core 90, through the slot 102 in the core, through the opening 118 in the piston 84, through the small groove 122, and into the channel 121. The first puller wire 64 is anchored in the channel 121 by means of a puller wire anchor 124, which preferably comprises a short piece of hypodermic stock that is fixedly attached, e.g., by crimping, to the proximal end of the first puller wire 64 after it has passed through the small groove 122. The puller wire anchor 124 has a diameter greater than the width of the small groove 122 and thus prevents the proximal end of the first puller wire 64 from being pulled through the small groove. The length of the opening 118 is limited such that, when the piston 84 is in its most distal position relative to the housing 86, the opening does not extend outside the housing. However, the opening 118 is preferably long enough so that the first puller wire 64 extends through the opening at an angle rather than bending or kinking.

Because the catheter body 12 is attached to the core 90, proximal movement of the piston 84 relative to handle housing 86 and core 90 causes proximal movement of the piston and first puller wire 64 relative to the catheter body 12. Such movement results in deflection of the intermediate section 14 in the direction of the side of the first off-axis lumen 30 through which the first puller wire extends.

As shown in FIG. 9, the second puller wire 65 is anchored at its proximal end to a threaded slide 100, which is disposed in the slot 102 of the core 90, by any suitable method. In the depicted embodiment, the slide 100 comprises a generally solid, generally rectangular piece of plastic with threading 101 along one surface. The slide 100 has a generally rectangular hole 103 in which the distal end of the second puller anchor 65 in anchored with a puller wire anchor 125, in a manner similar to the first puller wire 64, discussed above.

The threaded slide 100 is mounted within the slot 102 in the core 90 such that the threaded slide is prevented from rotating, but is able to move longitudinally within the slot, thus producing a relative lateral motion between the threaded slide and the core. The handle housing 86 has a window 104, through which the threaded surface 101 of the threaded slide 100 protrudes when the handle is assembled. The window has first and second window edges 118 and 120, which limit the lateral movement of the threaded slide 100.

A threaded sleeve 98 is mounted between first and second shoulders 106 and 108 on the handle housing 86. The threaded sleeve 98 has internal threading that engages the threads 101 of the threaded slide 100, such that rotation of the threaded sleeve causes the threaded slide to move longitudinally within the slot 102 in the core 90. Other arrangements for slidably mounting the threaded slide 100 within the handle housing 86 could also be used in accordance with the invention. For example, the threaded slide 100 could be mounted over or around the core 90 instead of within a slot in the core.

Because the proximal end of the second puller wire 65 is attached to the threaded slide 100 and the core 90 is attached to the catheter body 12, longitudinal movement of the threaded slide relative to the core results in corresponding movement of the second puller wire relative to the catheter body. Therefore, when the threaded sleeve 98 is rotated, the second puller wire 65 moves proximally relative to the catheter body 12, thus causing the straight distal region 40 of the mapping assembly 17 to also move relative to the catheter body and arc proximally or deflect. The deflection of the straight distal region 40 of the mapping assembly 17, in turn, causes the circular main region 39 of the mapping assembly to contract to thereby have a smaller diameter.

In one embodiment, the threaded sleeve 98 has a longitudinal slit and comprises a flexible material, such as delryn. To mount the threaded sleeve 98 over the handle housing 86, the sleeve is separated along the slit and fit over the housing, such that the sleeve is disposed between the shoulders 106 and 108 of the handle housing. Alternatively, the threaded sleeve 98 may be formed from two halves that are fit over the housing 86 and then affixed together, such as by weld, adhesive, a screw, a rivet or the like. In the depicted embodiment, a gripping sleeve 112 is mounted over the threaded sleeve 98 to aid in rotating the sleeve and provide comfort to the user. The gripping sleeve 112 may comprise a high friction surface, such as rubber. The gripping sleeve 112 also aides in holding the threaded sleeve 98 together when the sleeve is assembled on the handle housing 86.

In the depicted embodiment, the threaded sleeve 98 goes around the entire circumference of the handle housing 86. If desired the threaded sleeve 98 could be replaced with another rotatable member that extends around only a part of the circumference of the handle housing 86.

If desired, a fastener (not shown) can be provided to maintain the handle housing 86 in place over the core 90. A description of such an arrangement is provided in U.S. patent application Ser. No. 09/546,310 filed Apr. 10, 2000, entitled "Single Gear Drive Bi-Directional Control Handle for Steerable Catheter," the disclosure of which is incorporated herein by reference.

In use, a suitable guiding sheath is inserted into the patient with its distal end positioned at a desired mapping location. An example of a suitable guiding sheath for use in connection with the present invention is the Preface™ Braiding Guiding Sheath, commercially available from Cordis Webster (Diamond Bar, Calif.). The distal end of the sheath is guided into one of the atria. A catheter in accordance with the present invention is fed through the guiding sheath until its distal end extends out of the distal end of the guiding sheath. As the catheter is fed through the guiding sheath, the mapping assembly 17 is straightened to fit through the sheath. Once the distal end of the catheter is positioned at the desired mapping location, the guiding sheath is pulled proximally, allowing the deflectable intermediate section 14 and mapping assembly 17 to extend outside the sheath, and the mapping assembly 17 returns to its original shape due to the shape-memory of the support member 24. The mapping assembly 17 is then inserted into a pulmonary vein or other tubular region (such as the coronary sinus, superior vena cava, or inferior vena cava) so that the outer circumference of the generally circular main region 39 of the assembly is in contact with a circumference inside the tubular region. Preferably at least about 50%, more preferably at least about 70%, and still more preferably at least about 80% of the circumference of the generally circular main region is in contact with a circumference inside the tubular region.

The circular arrangement of the electrodes 36 permits measurement of the electrical activity at that circumference of the tubular structure so that ectopic beats between the electrodes can be identified. The size of the generally circular main region 39 permits measurement of electrical activity along a diameter of a pulmonary vein or other tubular structure of or near the heart because the circular main region has a diameter generally corresponding to that of a pulmonary vein or the coronary sinus. Additionally, because the main region 39 preferably does not form a flat circle, but instead is somewhat helical, as shown in FIG. 4, it is easier for the user to guide the mapping assembly 17 into a tubular region. If the circumference of the main region 39 of the mapping assembly 17 is larger than the circumference of the structure to be mapped, the mapping assembly can be contracted by longitudinal movement of the second puller wire 65 using the control handle 16, as described above.

The inventive handle is not limited to the above-described catheter design. The handle is also particularly useful for bi-directional catheters and other catheters having two puller wires for deflection of the distal end of the catheter body, i.e., the intermediate section. Such catheters are described in U.S. Pat. Nos. 6,171,277, 6,183,463, 6,198,974, 6,210,407, and 6,267,746, U.S. patent application Ser. No. 09/822,087, filed Mar. 30, 2001, "Steerable Catheter with a Control Handle Having a Pulley Mechanism," and U.S. patent application Ser. No. 09/846,732, filed Apr. 30, 2001, entitled "Asymmetrical Bidirectional Steerable Catheter," the disclosures of which are incorporated herein by reference. Other uses for the handle of the invention would be recognized by one skilled in the art.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter comprising:
   an elongated, flexible catheter body having proximal and distal ends and a lumen extending therethrough;
   an intermediate section at the distal end of the catheter body having proximal and distal ends and first and second off-axis lumens extending therethrough;
   a handle mounted at the proximal end of the catheter body, the handle comprising:
      a handle housing having proximal and distal ends and generally hollow interior, whereby the catheter body is attached to the handle housing,
      a first moveable member having a proximal end mounted in the interior of the handle housing and a distal end extending outside the handle housing, the first moveable member being longitudinally moveable relative to the handle housing, and
      a second moveable member mounted in the interior of the handle housing and longitudinally moveable relative to the handle housing; and
      a rotatable member mounted on the handle housing, whereby rotation of the rotatable member causes longitudinal movement of the second moveable member;
   a first puller wire extending through the catheter body and first off-axis lumen of the intermediate section, having a proximal end anchored to the first moveable member of the handle, and having a distal end anchored at or near the distal end of the catheter; and
   a second puller wire extending through the catheter body and second off-axis lumen of the intermediate section, having a proximal end anchored to the second moveable member of the handle, and having a distal end anchored at or near the distal end of the catheter.

2. The catheter of claim 1, wherein the distal end of the first puller wire is anchored to the intermediate section.

3. The catheter of claim 1, further comprising a generally circular mapping assembly mounted on the distal end of the intermediate section and having proximal and distal ends and an off-axis lumen extending therethrough, wherein the distal end of the second puller wire extends through the off-axis lumen of the mapping assembly and is anchored at or near the distal end of the mapping assembly.

4. The catheter of claim 1, wherein the first moveable member and second moveable member are capable of simultaneously moving proximally relative to the handle housing.

5. The catheter of claim 1, wherein the rotatable member has a threaded inner surface that mates with a threaded surface of the second moveable member.

6. The catheter of claim 5, wherein the catheter handle further comprises a core mounted in the interior of the handle housing, the core having a longitudinal slot therethrough in which the second moveable member is slidably mounted.

7. The catheter of claim 1, wherein the catheter handle further comprises a core mounted in the interior of the handle housing, the core having a longitudinal slot therethrough in which the second moveable member is slidably mounted.

8. The catheter of claim 7, wherein the first moveable member is generally tubular and is mounted in surrounding relation to a portion of the core.

9. The catheter of claim 3, wherein longitudinal movement of the first puller wire results in deflection of the intermediate section, and longitudinal movement of the second puller wire results in contraction of the generally circular mapping assembly.

* * * * *